US00PP21124P2

(12) United States Plant Patent
Hofmann

(10) Patent No.: US PP21,124 P2
(45) Date of Patent: Jun. 29, 2010

(54) ***BIDENS* PLANT NAMED 'FISBICOM'**

(50) Latin Name: *Bidens ferulifolia*
Varietal Denomination: Fisbicom

(75) Inventor: Birgit Christa Hofmann, Ruedesheim (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/384,592

(22) Filed: Apr. 7, 2009

(51) Int. Cl.
*A01H 5/00* (2006.01)

(52) U.S. Cl. ..... Plt./410

(58) Field of Classification Search ..... Plt./410
See application file for complete search history.

*Primary Examiner*—Kent L Bell
(74) *Attorney, Agent, or Firm*—S. Matthew Edwards

(57) ABSTRACT

A new *Bidens* plant named 'Fisbicom', particularly distinguished by the yellow inflorescence color, relatively small inflorescence with 5 ray florets, medium to deep green foliage, medium or weak to medium, vigor, very well branching, tight, mounding, relaively low plant habit, and early to medium flowering response.

1 Drawing Sheet

Latin name of the genus and species of the plant claimed: *Bidens ferulifolia.*

Varietal denomination: 'Fisbicom'.

BACKGROUND OF THE NEW PLANT

The present invention comprises a new *Bidens* plant, botanically known as *Bidens ferulifolia* and hereinafter referred to by the variety name 'Fisbicom'.

'Fisbicom' is a product of a planned breeding program. The new cultivar has bright yellow, single-type inflorescences, free branching, and compact plant habit.

'Fisbicom' originated from a hybridization made in the summer of 2005 in a controlled breeding program in Hillscheid, Germany. The female parent was an unpatented hybrid seedling identified as 'K05-1047-1' with yellow inflorescences with 5 ray florets and with very compact plant habit.

The male parent of 'Fisbicom' was an unpatented hybrid seedling identified as 'K05-1018-1' with large yellow inflorescences with 8 ray florets and with vigorous growth habit.

'Fisbicom' was selected as one flowering plant within the progeny of the stated cross in the spring of 2006 in a controlled environment in Hillscheid, Germany.

The first act of asexual reproduction of 'Fisbicom' was accomplished when vegetative cuttings were used from the initial selection in the summer of 2006 in a controlled environment in Hillscheid, Germany.

Horticultural examination of plants grown from cuttings of the plant initiated in March 2007 in Hillscheid, Germany, and continuing thereafter, has demonstrated that the combination of characteristics as herein disclosed for 'Fisbicom' are firmly fixed and are retained through successive generations of asexual reproduction.

'Fisbicom' has not been observed under all possible environmental conditions. The phenotype may vary significantly with variations in environment such as temperature, light intensity and day length.

Plant Breeder's Rights for this cultivar were applied for in Canada on May 1, 2008 and in the European Union on Jun. 2, 2008. 'Fisbicom' has not been made publicly available more than one year prior to the filing of this application.

BRIEF DESCRIPTION OF DRAWING

The accompanying photographic drawing taken in mid February 2007 show typical inflorescence and foliage characteristics of 'Fisbicom' with colors being as true as possible with an illustration of this type.

DETAILED BOTANICAL DESCRIPTION

Figure 1:
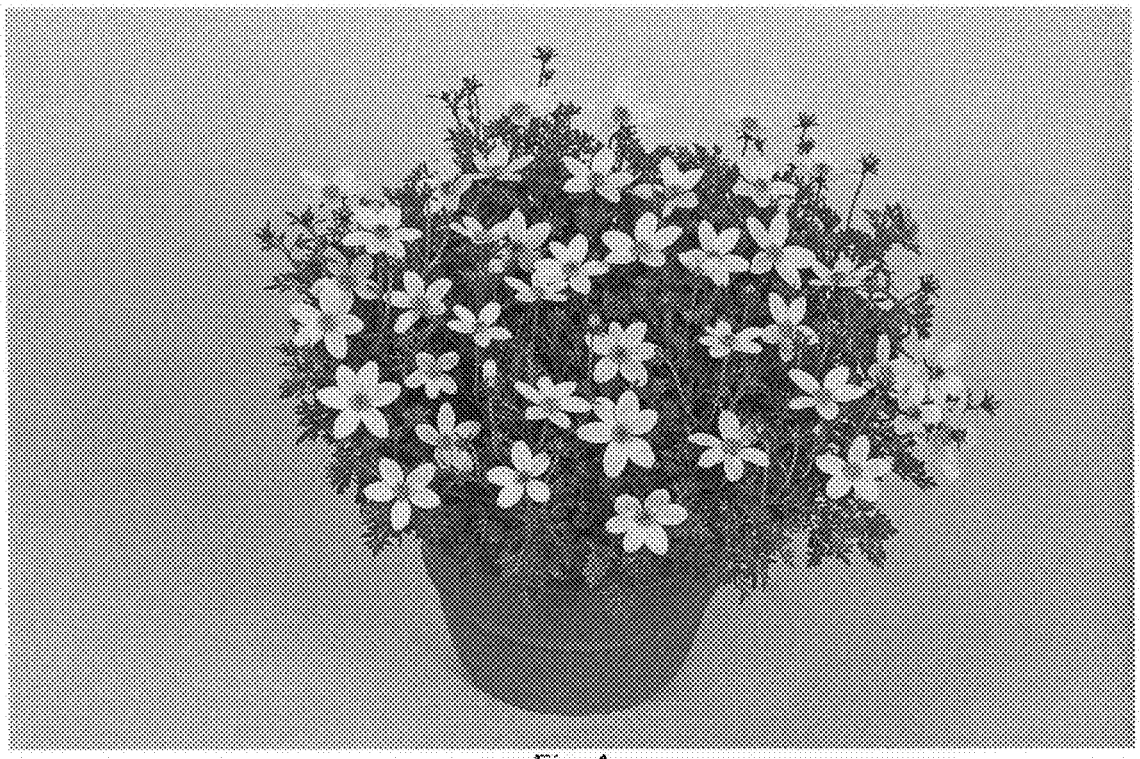
FIG. 1 shows a flowering plant in a 12 cm container, 3-4 months old.
Figure 2:
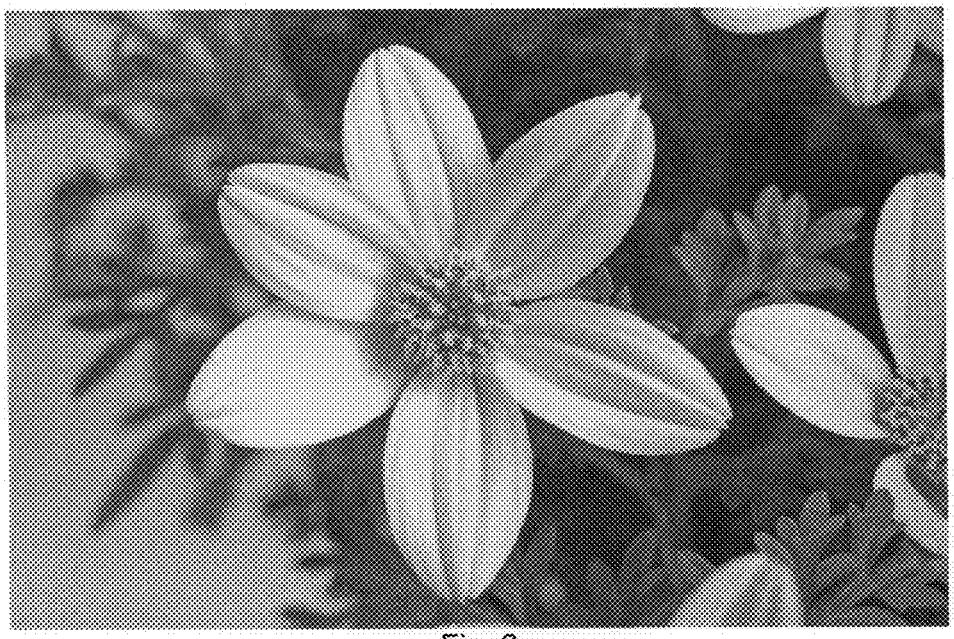
FIG. 2 is a close view of a single inflorescence.

The measurements were taken in Hillscheid, Germany, in early May 2007 on plants that were growing in the greenhouse in 12 cm pots. The plants were about 10 weeks old and had been grown at relatively cool temperatures.

Color chart used: Royal Horticultural Society Colour Chart (R.H.S.) 2001.

BRIEF SUMMARY OF INVENTION

The following observations, measurements, and comparisons describe plants grown indoors and outdoors in Hillscheid, Germany. The following traits have been repeatedly observed and are determined to be basic characteristics of the new variety. The combination of these characteristics distinguishes this *Bidens* as a new and distinct variety.

1. Bright yellow inflorescence color
2. Relatively small inflorescences with 5 ray florets
3. Medium to deep green foliage, dissected leaves
4. Freely branching
5. Compact, mounding, low and cushion-like habit
6. Early to medium flowering response

DIFFERENCES BETWEEN THE NEW VARIETY 'FISBICOM' AND SIMILAR VARIETIES

In comparison to 'Fisbimex', U.S. Plant Pat. No. 19,164, 'Fisbicom' has smaller flowers with only 5 rays ('petals'), shorter branches and generally much more compact plant habit with the flowers closer to the foliage canopy.

In comparison to 'Golden Star', U.S. Plant Pat. No. 12,589, 'Fisbicom' has similar flowers, but plant habit is more compact with lower foliage canopy and shorter flowering stems.

Plant:

*Form, growth and habit.*—Herbaceous, cultivated as an annual plant, bushy, mounding, tight structure.

*Plant height (inflorescence included).*—17 cm.

*Plant width.*—31 cm.

*Structure of branching.*—Freely, lateral branches are developed at nearly every node.

*Number of branches.*—Approximately 50.

*Time to produce a saleable plant.*—7-8 weeks.

Stem:

*Color of young stems or shoot tips.*—Light green, RHS 143B.

*Color of lower and middle part.*—RHS 146A to RHS 197A, a little variable.

*Length of stem.*—9-15 cm.

*Diameter.*—3 mm at middle part.

*Length of internodes.*—1.5-2.5 cm.

*Texture.*—Fine pubescence.

Foliage:

*Arrangement.*—Opposite, decussate.

*Immature leaf, color upper surface.*—RHS 137D.

*Immature leaf, color lower surface.*—RHS 143C.

*Mature leaf, color upper surface.*—RHS 137B to 137C.

*Mature leaf, color lower surface.*—RHS 143C.

*Length.*—2.7-3.4 cm.

*Width.*—2.5-2.7 cm.

*Shape.*—Roughly deltoid, pinnatisect.

*Base shape.*—Obtuse to nearly truncate.

*Apex shape.*—Acute.

*Margin.*—Deeply incised.

*Texture upper surface.*—Smooth, glabrous, somewhat glossy.

*Texture lower surface.*—Sparse hair, mainly along the veins.

Petiole:

*Petiole color, upper side.*—RHS 137D.

*Petiole color, lower side.*—RHS 145A.

*Petiole length.*—3-4 mm.

*Diameter of petiole.*—1-2 mm.

*Texture.*—Smooth, sparse hair along the margins.

Inflorescence:

*Start of flowering.*—7-8 weeks after potting of rooted cuttings.

*Duration of flowering.*—Continuous flowering throughout the summer.

*Type.*—Solitary inflorescences, terminal, composite type.

*Shape.*—Round, semi-spherical disc surrounded by 5 ray florets, thus resembling a single-type flower.

*Whole diameter.*—3.5-3.8 cm.

*Depth.*—0.6-0.7 cm.

*Number of ray florets.*—Usually 5.

*Diameter of disc.*—0.9-1.0 cm.

*Number of florets per disc.*—About 25-30.

*Fragrance.*—None.

Peduncle:

*Length of peduncle.*—3.5-5.0 cm.

*Diameter.*—1-1.5 cm.

*Texture.*—Furrowed near the inflorescence base, densely covered with short hair.

*Color.*—RHS 145A.

Ray florets:

*Form and shape.*—Elliptical.

*Apex.*—Obtuse to slightly dentate or praemorse.

*Base.*—Fused.

*Margins.*—Entire.

*Length.*—1.2-1.3 cm.

*Width.*—0.7-0.9 cm.

*Color of upper surface.*—Yellow, RHS 12A, uniform.

*Color of lower surface.*—RHS 9B.

*Texture.*—Glabrous, smooth, apart from shallow veins.

Disc florets:

*Form and shape.*—Tubular.

*Length.*—3 mm.

*Width at apex.*—1 mm.

*Color of surface, near apex.*—Yellow, RHS 5B, fading towards base.

Inflorescence bud:

*Shape.*—Initially round to ovoid, elongates with the development of the ray florets.

*Color.*—RHS 9A.

*Length.*—7-8 mm.

*Width.*—5-7 mm.

Receptacle:

*Shape.*—Semi-spherical.

*Diameter.*—5-6 mm.

*Depth.*—3-4 mm.

*Number of phyllaries.*—Approximately 9.

*Color.*—Deep green, RHS 137A.

*Shape.*—Narrow elliptical.

*Length.*—Up to 5 mm.

*Width.*—1-2 mm.

*Shape of apex.*—Obtuse, or broadly acute.

*Base.*—Attenuate.

*Margin.*—Entire.

*Texture of upper surface.*—Upper surface glossy, glabrous.

*Texture of lower surface.*—Sparse, very short hairs.

Reproductive organs:

Gynoecium:

*Pistil.*—One.

*Length.*—7 mm.

*Style length.*—4 mm.

*Stigma shape.*—Cleft, reflexed.

*Stigma color.*—RHS 13C.

Androecium:

*Number of anthers.*—One androecium, probably formed by fused stamen.

*Length of anthers.*—4 mm.

*Anther color.*—RHS 200A.

*Pollen amount.*—Moderate.

*Color of pollen.*—RHS 12A.

Fertility/seed set.—Not observed.

Disease resistance: Disease resistance or susceptibility has not been observed on this hybrid.

What is claimed is:

1. A new and distinct variety of *Bidens* plant named 'Fisbicom', substantially as illustrated and described herein.

* * * * *